(12) United States Patent
Palero et al.

(10) Patent No.: US 10,946,192 B2
(45) Date of Patent: Mar. 16, 2021

(54) DEVICE FOR RADIO FREQUENCY SKIN TREATMENT

(71) Applicant: KONINKLIJKE PHILIPS N.V., Eindhoven (NL)

(72) Inventors: Jonathan Alambra Palero, Eindhoven (NL); Marco Baragona, Eindhoven (NL); Martin Jurna, Eindhoven (NL); Babu Varghese, Eindhoven (NL); Hendrik Halling Van Amerongen, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 394 days.

(21) Appl. No.: 15/568,924

(22) PCT Filed: Apr. 21, 2016

(86) PCT No.: PCT/EP2016/058817
§ 371 (c)(1),
(2) Date: Oct. 24, 2017

(87) PCT Pub. No.: WO2016/173909
PCT Pub. Date: Nov. 3, 2016

(65) Prior Publication Data
US 2018/0110977 A1  Apr. 26, 2018

(30) Foreign Application Priority Data
Apr. 28, 2015  (EP) .................................... 15165369

(51) Int. Cl.
*A61N 1/32* (2006.01)
*A61B 18/14* (2006.01)
(Continued)

(52) U.S. Cl.
CPC .............. *A61N 1/328* (2013.01); *A61B 18/14* (2013.01); *A61N 1/06* (2013.01); *A61N 1/403* (2013.01);
(Continued)

(58) Field of Classification Search
CPC combination set(s) only.
See application file for complete search history.

(56) References Cited

U.S. PATENT DOCUMENTS 4,605,012 A  8/1986  Ringeisen
5,700,176 A  12/1997  Potter
(Continued)

FOREIGN PATENT DOCUMENTS

| WO | 2008059072 A1 | 5/2008 |
| WO | 2012023129 A1 | 2/2012 |
| WO | 2012029065 A2 | 3/2012 |

*Primary Examiner* — Joseph A Stoklosa
*Assistant Examiner* — Adam J Avigan

(57) ABSTRACT

The invention relates to a device (100) for RF skin treatment, comprising an active electrode (1) arranged on an operational side (15) of the device and having a first skin contact surface for contact with a skin of a user, which first skin contact surface has a largest cross-sectional dimension smaller than or equal to 2 mm. The device comprises a return electrode (2) arranged on the operational side (15) of the device and having a second skin contact surface for contact with the skin of the user, wherein an area of the second skin contact surface is at least five times larger than an area of the first skin contact surface. An RF generator (21) is arranged to supply an RF treatment voltage between the active electrode (1) and the return electrode (2) so as to heat a skin region below the active electrode, wherein the RF treatment voltage has a frequency in a range of 100 MHz-3 GHz. By using a frequency of the RF treatment voltage in said range, a depth of thermal lesions voltage is considerably increased (Continued)

as compared to RF skin treatment devices using a comparable RF treatment voltage, but at a much lower frequency.

12 Claims, 5 Drawing Sheets

(51) Int. Cl.
*A61N 1/40* (2006.01)
*A61N 1/06* (2006.01)
*A61B 18/00* (2006.01)
*A61B 18/16* (2006.01)

(52) U.S. Cl.
CPC ............... *A61B 2018/0016* (2013.01); *A61B 2018/0047* (2013.01); *A61B 2018/00452* (2013.01); *A61B 2018/00767* (2013.01); *A61B 2018/1425* (2013.01); *A61B 2018/162* (2013.01)

(56) References Cited

U.S. PATENT DOCUMENTS

| | | | |
|---|---|---|---|
| 6,228,078 | B1 | 5/2001 | Eggers |
| 2009/0018628 | A1 | 1/2009 | Burns |
| 2009/0299361 | A1* | 12/2009 | Flyash ............... A61N 5/00 606/33 |
| 2011/0118722 | A1* | 5/2011 | Lischinsky ............ A61B 18/12 606/33 |
| 2012/0029498 | A1 | 2/2012 | Branovan |
| 2012/0253416 | A1* | 10/2012 | Erez ............... A61H 9/0057 607/3 |
| 2013/0123765 | A1 | 5/2013 | Zarsky |
| 2013/0289679 | A1* | 10/2013 | Eckhouse ............. A61N 1/06 607/102 |
| 2014/0024960 | A1 | 1/2014 | Smith |
| 2014/0249609 | A1* | 9/2014 | Zarsky ............... A61N 1/40 607/102 |

* cited by examiner

DEVICE FOR RADIO FREQUENCY SKIN TREATMENT

This application is the U.S. National Phase application under 35 U.S.C. § 371 of International Application No. PCT/EP2016/058817, filed on Apr. 21, 2016, which claims the benefit of International Application No. 15165369.8 filed on Apr. 28, 2015. These applications are hereby incorporated by reference herein.

FIELD OF THE INVENTION

The invention relates to a device for skin treatment, in particular radio frequency (RF) treatment of human skin. The device is primarily suitable for fractional RF skin treatment, in particular for skin rejuvenation.

BACKGROUND OF THE INVENTION

Radio frequency (RF) is conventionally used in both the professional and the home-use aesthetic market for skin tightening. The ability of large-volume heating at the dermal skin level has made the radio frequency technology a standard for skin tightening and for treating skin laxity. Compared to laser-based skin treatment devices, RF skin treatment devices have a relatively lower cost price and can provide treatment of larger volumes of the skin and treatment of deeper skin tissue. Additionally, RF energy dissipation by skin tissue does not rely on absorption of light by chromophores, so that tissue pigmentation does not interfere with the delivery of energy.

The basic principle of RF energy delivery at the skin surface to tissue is that an alternating RF current is applied in a closed circuit with the skin. Skin tissue impedance directly affects the extent of the heating. RF current propagates more easily through skin tissues with high electrical conductivity (i.e. low electrical resistance), while skin tissues with high electrical resistance (i.e. high impedance and low electrical conductivity) are poor conductors of RF energy. The RF energy takes the path of least electrical resistance through the skin tissue and is dissipated as thermal energy primarily due to molecular vibrations.

A growing application for RF skin treatment, beyond skin tightening, is skin rejuvenation, wherein fractional thermal lesions are simultaneously created in the skin using one or more small active electrodes. Recently, different professional devices have been launched on the aesthetic market addressing skin rejuvenation with a radio frequency device. Skin rejuvenation is a combination of different consumer benefits, such as even skin tone, reduction of pigmentation spots, improved radiance and texture, and the reduction of fine lines. In this treatment, the energy is used to primarily damage the stratum corneum and the epidermis, including the dermal-epidermal junction, and possibly the top part of the dermis. Traditionally, skin rejuvenation treatments are done by ablative or non-ablative settings of a laser wavelength highly absorbed by water, wherein ablative treatments vaporize the skin and create hollow pillars in the skin, and non-ablative treatments heat the skin to a temperature between 65-100° C. to initiate cell necrosis, collagen denaturation and contraction, and eventually collagen remodeling.

The advantage of fractional treatments is mainly due to the ability to create microscopic thermal lesions that are small enough not to induce tissue scarring and to heal relatively fast. According to the literature, the size of fractional thermal lesions should be less than 0.5 mm to avoid scarring and other side effects, e.g. infection. On the other hand, the efficacy of fractional treatments is also dependent on the depth of the microscopic thermal lesions, because the treatment should also result in thermal denaturation of the collagen in the dermis to cause dermal regeneration and rejuvenation. Thus, the ideal case is when the fractional treatment creates single thermal lesions that have a small cross-sectional area and a large penetration depth, i.e. thermal lesions that have a large depth-to-width ratio.

To improve the safety of RF skin treatment devices, very recently a device has been proposed for home use, which comprises a bi-polar electrode configuration. With this device, a very small active inner electrode and a larger outer return electrode surrounding the inner electrode both make contact with the skin, and an RF treatment voltage less than 50 V is applied to the skin at a frequency between 1 and 40 MHz. With this RF treatment device, the thermal penetration depth of the RF energy is about 0.5 times the diameter of the active inner electrode, so that in practice thermal lesions with a penetration depth of about 200 microns are achieved by means of active inner electrodes having a diameter of about 400 microns.

WO 2012/023129 A1 discloses a fractional RF skin treatment device having active electrodes with a diameter in a range between 100 and 2000 microns surrounded by much larger return electrodes. The device applies an RF treatment voltage in a range between 50 and 400 Volts at a frequency in a range between 350 kHz and 10 MHz.

US 2014/0249609 A1 discloses a system for applying electromagnetic energy through an epidermal skin layer to the underlying dermal and/or sub-dermal tissue and underlying collagen tissue to cause acceleration of lipolysis and collagen remodeling. The system includes one or more capacitive applicators to create, without contacting the skin, an electromagnetic field crossing through the skin. The applicators are placed on top of spacers made of a dielectric or electrically non-conductive material to set a separation distance between the applicators and the skin. The applicators may be bipolar electrodes, where the electrodes alternatively have an active and return function. The system comprises a high-frequency generator which may generate an electromagnetic field, preferably at 13.56 MHz, 27.12 MHz, 40.68 MHz, or 2.45 GHz in order to avoid creating radio interference.

US 2009/0018628 A1 discloses an apparatus for treating skin conditions by delivering high-frequency energy across large tissue areas. The apparatus includes a handpiece, a treatment tip releasably coupled with the handpiece, and an energy delivery member carried by the treatment tip. The energy delivery member is electrically coupled with a high-frequency power supply having an operating frequency in the radio-frequency region of the electromagnetic spectrum, in particular in a range of several hundred kHz to about 60 MHz, to impart a therapeutic effect to treat target tissue beneath a patient's skin surface. The apparatus further comprises a passive return electrode, electrically coupled with a negative voltage polarity terminal of the high-frequency power supply, which is physically attached to a body surface of the patient remote from the treatment tip.

U.S. Pat. No. 6,228,078 B1 discloses a method for treatment of an external body surface of a patient, wherein an electrode terminal is positioned in close proximity to a target site on the external body surface, and wherein high-frequency electrical energy is applied to the electrode terminal sufficient to remove a layer of the external body surface and to effect contraction of collagen fibers within tissue underlying said layer. The electrode terminal comprises an electrode array distributed over a contact surface of the terminal and a return electrode. The voltage applied between the return electrode and the electrode array is at radio-frequency level, typically between about 5 kHz and 20 MHz, more preferably less than 350 kHz, and most preferably between about 100 kHz and 200 kHz.

WO 2012/029065 A2 discloses a self-operated device for treating a skin of a patient, comprising a substrate having a first side and a second side, a plurality of RF electrodes arranged in said substrate, said RF electrodes being configured to emit RF radiation from said first side to the surface of said skin, at least one RF generator configured to generate pulses of current to said RF electrodes, and a control unit connected to said at least one RF generator, said control unit being adapted to control the operation of said RF electrodes, wherein said control unit is adapted to control the operation of said RF electrodes according to a predetermined treatment protocol, such that the same activates or deactivates at least one of said RF electrodes at any predetermined time interval according to a predetermined pattern so as to achieve a particular therapeutic result. The device operates at predetermined frequencies between about 1 Hz and about 100 MHz.

SUMMARY OF THE INVENTION

It is an object of the invention to provide an improved device for RF skin treatment which generates non-ablative fractional thermal lesions in skin tissue having an increased penetration depth and an increased depth-to-width ratio as compared to known RF skin treatment devices, while using relatively low RF treatment voltages.

According to a first aspect, the invention provides a device for RF skin treatment, comprising an active electrode arranged on an operational side of the device and having a first skin contact surface for contact with a skin of a user, which first skin contact surface has a largest cross-sectional dimension smaller than or equal to 2 mm. The device further comprises a return electrode arranged on the operational side of the device and having a second skin contact surface for contact with the skin of the user, wherein an area of the second skin contact surface is at least five times larger than an area of the first skin contact surface. The device further comprises an RF generator arranged to supply an RF treatment voltage between the active electrode and the return electrode so as to heat a skin region below the active electrode, wherein the RF treatment voltage has a frequency in a range of 100 MHz-3 GHz.

According to the invention, a much higher frequency of the RF treatment voltage is used as compared to fractional RF skin treatment devices according to the state of the art. The result of this relatively high frequency is a deeper thermal penetration depth of the RF energy below the active small-size electrodes of the bi-polar electrode configuration, resulting in deeper thermal lesions below the active electrodes, which also have an improved, i.e. a higher depth-to-width ratio.

In a preferred embodiment of the device according to the invention, the frequency of the RF treatment voltage is in a range of 500 MHz-1.5 GHz. Simulations have shown that an optimum penetration depth and an optimum depth-to-width ratio of the fractional thermal lesions below the active electrode is achieved by using frequencies in a range of 500 MHz-1.5 GHz. For an active electrode with a diameter of 200 microns applying RF energy pulses with a frequency of 1 GHz and a pulse duration of 50 ms, the thermal lesion depth is about 1.5 times the thermal lesion depth achieved with comparable RF energy pulses with a frequency of 1 MHz.

Another advantage of the use of a higher frequency of the RF treatment voltage is an increased efficiency of the conversion of the RF energy into heat in the skin tissue, which results in a decrease of the RF treatment voltage required to achieve a certain temperature in the skin tissue.

In an embodiment of the device according to the invention, the RF treatment voltage has a root mean square (RMS) value of less than 50 V. In a preferred embodiment, the RF treatment voltage is below 20 V.

In an embodiment of the device according to the invention, the active electrode is fully surrounded by the return electrode on the operational side of the device. In this embodiment, the active electrode is referred to as inner electrode and the return electrode as outer electrode. The inner electrode may be annular (i.e. ring shaped) or disc shaped (i.e. a filled circle). The inner electrode may also be non-circular, for example rectangular, having a largest cross-sectional dimension smaller than or equal to 2 mm, as mentioned above. In the following, instead of the expression 'largest cross-sectional dimension', the word 'size' is also used.

The proposed combination of the small inner electrode size and the relatively high frequency of the RF treatment voltage results in the formation of thermal lesions below the inner electrode that are sufficiently deep for effective skin rejuvenation and sufficiently narrow to enable fast recovery of the skin.

The inner electrode and the outer electrode are configured to simultaneously contact the skin during the treatment. The first skin contact surface of the inner electrode does not need to be flat. It may be curved. This also applies to the second skin contact surface of the outer electrode.

In an embodiment of the device according to the invention, a ratio between the area of the second skin contact surface of the return electrode and the area of the first skin contact surface of the active electrode is greater than 10. In this embodiment, undesired heating of the skin region below the return electrode is further reduced or even prevented.

In an embodiment of the device according to the invention, the device comprises an electronic controller configured to receive an input signal related to a desired lesion depth or a desired lesion depth-to-width ratio, and to control the frequency of the RF treatment voltage depending on the desired lesion depth or the desired lesion depth-to-width ratio. In this way, a user is able to set or control the desired lesion depth and/or the desired lesion depth-to-width ratio.

The device according to the invention as described above may be used in the treatment of skin, such as skin rejuvenation.

Further preferred embodiments of the device according to the invention and the use thereof are given in the appended claims.

BRIEF DESCRIPTION OF THE DRAWINGS

These and other aspects of the invention will be apparent from and elucidated further with reference to the embodiments described by way of example in the following description and with reference to the accompanying drawings, in which FIG. 1 schematically shows an embodiment of a device for RF skin treatment according to the invention, comprising an active electrode and a return electrode.

The figures are purely diagrammatic and not drawn to scale. In the Figures, elements which correspond to elements already described may have the same reference numerals.

DETAILED DESCRIPTION OF THE EMBODIMENTS

Figure 1:
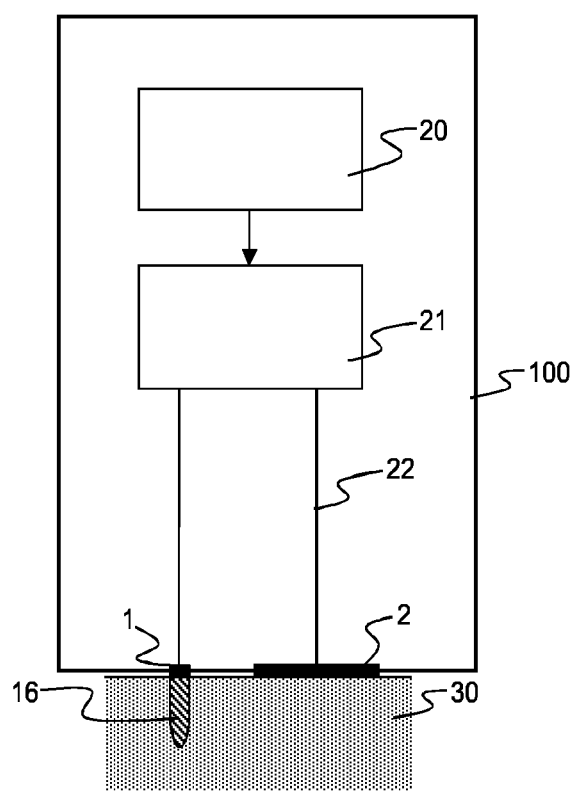

FIG. 1 schematically shows a device 100 for RF skin treatment comprising an active electrode 1 and a return electrode 2. The device 100 also comprises an electronic controller 20, a radio frequency (RF) generator 21 connected by electric cables 22 to the active electrode 1 and return electrode 2. The RF generator 21 may comprise a generating module producing RF signals and an amplifier for amplifying the RF signals. The electronic controller 20 may comprise an impedance detection system to measure skin impedance between the active electrode 1 and the return electrode 2, and a feedback controller based on the measured impedance. The electronic controller 20 may further comprise a feedback adjuster for the applied RF treatment voltage or the applied pulse duration of the RF treatment voltage pulses.

In FIG. 1, the active electrode 1 and the return electrode 2 are placed on a part of skin 30. A first skin contact surface of the active electrode 1 is relatively small. A largest cross-sectional dimension of the first skin contact surface of the active electrode 1 is equal to or smaller than 2 mm.

Once the active electrode 1 and the return electrode 2 are placed on the skin 30 and the device 100 is activated, an RF current will flow through the skin 30. Due to the RF current, a thermal zone 16 in a skin region below the small-area active electrode 1 is generated. When the thermal zone 16 is heated sufficiently long, a small thermal lesion will be created in the skin tissue.

According to the invention, the frequency of the applied RF treatment voltage is in a range of 100 MHz 3 GHz. A preferred range of the frequency of the RF treatment voltage is 500 MHz-1.5 GHz. Due to the electrode configuration and the frequency of the RF treatment voltage used, the thermal lesions generated immediately below the active electrode 1 are relatively deep and have an optimum depth-to-width ratio.

The present invention is based on the new insight that, in fractional RF skin treatments, there is a range of frequencies of the RF treatment voltage for which the thermal penetration depth and the depth-to-width ratio of the thermal lesions are optimal. Simulations were done for complex skin structures that include all thermal and electrical properties of the different layers of the skin, including stratum corneum, viable epidermis and dermis. Simulations using a frequency of the RF treatment voltage of 1 GHz, applied with a pulse duration of 50 ms, have shown an improvement of the penetration depth of the thermal lesions by a factor of 1.5 as compared to a frequency of 1 MHz. The depth-to-width ratio was also significantly improved as compared to the state of the art devices.

Figure 2:
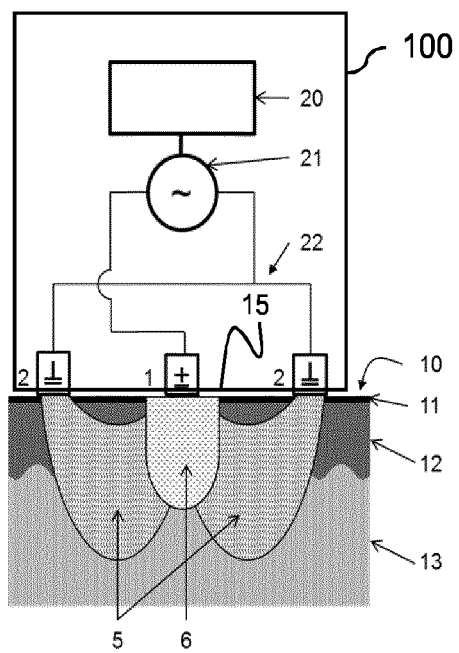
FIG. 2 is a schematic cross section of another embodiment of a device for RF skin treatment according to the invention.

FIG. 2 is a schematic cross section of another embodiment of a device 100 for RF skin treatment according to the invention. In this exemplary embodiment, the device 100 comprises an active inner electrode 1 and a ring-shaped outer return electrode 2, both arranged on an operational side 15 of the device 100. The device 100 also comprises an electronic controller 20, and a radio frequency (RF) generator 21 connected by electric cables 22 to the inner and outer electrodes 1 and 2. In the situation shown in FIG. 2, the inner and outer electrodes 1, 2 are positioned on the skin surface 10, and the skin comprises the stratum corneum 11, the epidermis 12 and the dermis 13. When powered, the inner and outer electrodes 1, 2 create electric RF field lines 5 within the skin and, due to the applied RF treatment voltage in combination with the skin impedance, heat is deposited within the skin, thereby creating a non-ablative thermal lesion 6 immediately below the inner electrode 1 when the temperature reaches a value between 65° C. and 100° C. The electronic controller 20 is arranged to control the RF generator 21. The RF generator 21 may provide an RF treatment voltage being lower than 50 V. In preferred embodiments, the RF treatment voltage may even be lower than 20 V.

In an embodiment, the electronic controller 20 is configured to receive an input signal related to a desired lesion depth or a desired lesion depth-to-width ratio, and to control the frequency of the RF treatment voltage depending on the desired lesion depth or the desired lesion depth-to-width ratio. The desired lesion depth or lesion depth-to-width ratio may be set by the user by means of an interface arranged in the device 100 and configured to process input from the user. The interface may e.g. be a touch-sensitive screen operated by a processing module which is programmed to instruct the user to input certain values for the desired lesion depth or the lesion depth-to-width ratio. The inputted information may then be converted to a certain frequency of the RF treatment voltage, using for example a look-up table stored in a memory of the device 100.

Figure 3:
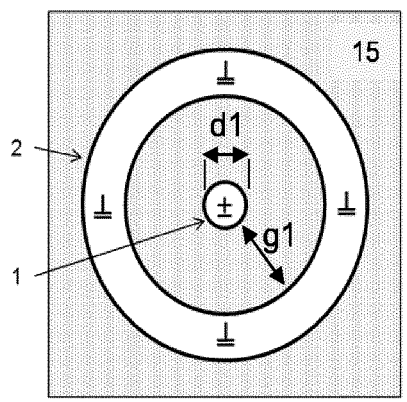
FIG. 3 shows a top view of an electrode configuration of the device of FIG. 2, wherein an inner electrode is fully surrounded by a ring-shaped outer electrode.

FIG. 3 shows a top view of the electrode configuration of the device of FIG. 2, wherein the active inner electrode 1 is fully surrounded by the ring-shaped outer return electrode 2. The inner electrode 1 is located in the center of the ring-shaped return electrode 2. The specific electrode configuration of the active inner electrode 1 and the outer return electrode 2, shown in FIG. 3, is called the centro-symmetric electrode configuration. In a preferred embodiment, the first skin contact surface of the inner electrode 1 has a diameter $d_1$ smaller than 1 mm, more preferably between 200-500 µm. The distance between the inner and outer electrodes 1 and 2 is referred to as the gap $g_1$. The gap $g_1$ is defined as being the minimal distance between a point on the outer edge of the inner electrode 1 and a point on the inner edge of the outer electrode 2. In an embodiment, the gap $g_1$ is greater than 0.1 mm, but it may also be greater than 0.2 mm.

To create multiple lesions at the same time, the device 100 may comprise a plurality of active electrodes and one or more return electrodes. Each of the plurality of active electrodes may be activated separately and at different moments in time. Alternatively, all active electrodes may be activated simultaneously.

In an embodiment, the device comprises a plurality of active electrodes, wherein each of the plurality of active electrodes is fully surrounded by a return electrode. The device may have more than one return electrode, wherein the return electrodes may border each other so as to form a lattice structure, or wherein the return electrodes may just be electrically coupled. A lattice structure of return electrodes will require less wiring from the RF generator to the return electrodes. Furthermore, a lattice structure of return electrodes enables more electrodes to be arranged on the same surface area as compared to an electrode configuration with separated return electrodes.

The device 100 can be used to create fractional thermal lesions in the skin tissue so as to rejuvenate the skin. Because of the relatively low RF treatment voltages (less than 75 V), the device is very suitable for home-use without the need for professional assistance.

Numerical simulations have shown that an optimum penetration depth and an optimum depth-to-width ratio of the fractional thermal lesions are achieved for frequencies of the RF treatment voltage in the range of 500 MHz-1.5 GHz. For an active electrode with a diameter of 200 micron applying RF treatment voltage pulses at 1 GHz with a pulse duration of 50 ms, the thermal lesion depth is about 1.5 times the thermal lesion depth for comparable RF treatment voltage pulses with a frequency of 1 MHz. It is further preferred to apply fractional RF skin treatment either without using any coupling gel or using a coupling gel with an impedance matched to the skin impedance.

Simulations were performed using different circumstances: a) on dry skin, which in practice implies the application of RF energy to the skin via a low-conductive contact gel or without any contact gel; b) on wet skin, which implies the application of RF energy to the skin via an electrically high-conductive contact gel; and c) on dry skin and monopolar, which in practice implies the application of RF energy without any contact gel, wherein the return electrode 2 is positioned relatively far away (e.g. more than 3 mm) from the active electrode 1.

Figure 4:
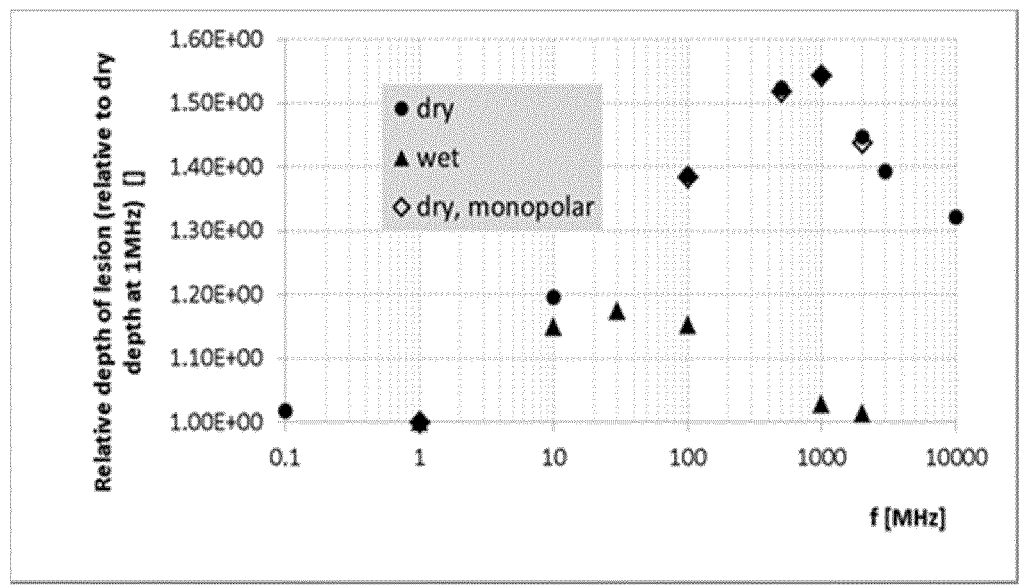
FIG. 4 shows a graph of simulation results of the thermal lesion depth as a function of the frequency of the RF treatment voltage.
Figure 5:
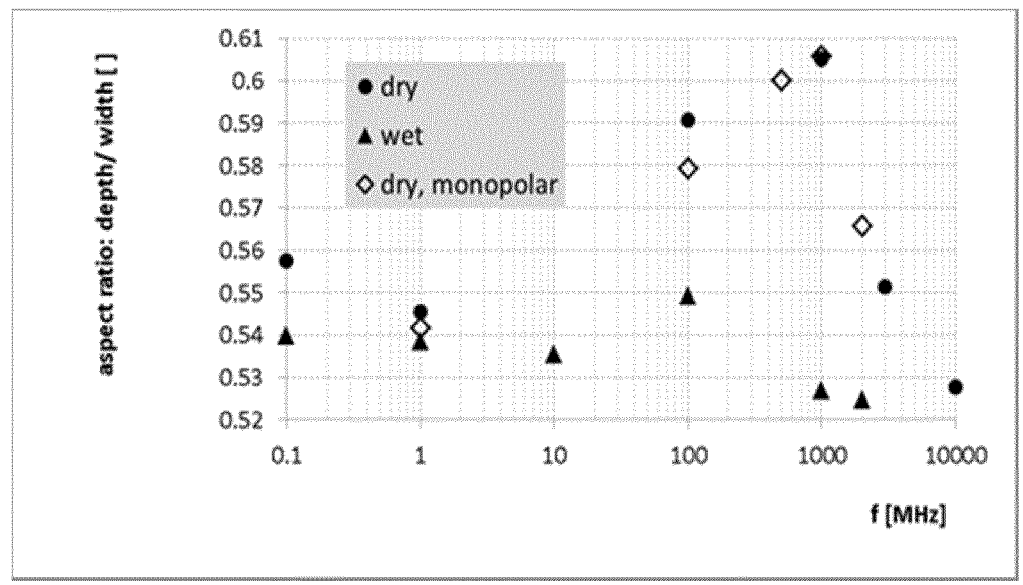
FIG. 5 shows a graph of the depth-to-width ratio of the thermal lesion as a function of the frequency of the RF treatment voltage.

FIG. 4 shows a graph of simulation results of the thermal lesion depth as a function of the frequency of the RF treatment voltage, including lower frequencies of about 1 MHz. FIG. 5 shows a graph of the depth-to-width aspect ratio of the thermal lesions as a function of the frequency of the RF treatment voltage. Based on the results shown in FIGS. 4 and 5, a preferred range of the frequency of the RF treatment voltage for achieving a relatively deep penetration depth of the thermal lesions and an optimal depth-to-width aspect ratio of the thermal lesions can be defined. This preferred range of the frequency is 100 MHz-3 GHz, and more preferably 500 MHz-1.5 GHz. Moreover, it is preferred to apply fractional RF skin treatment either without using any coupling gel or using a coupling gel with an electrical impedance matched to the electrical impedance of the skin.

Figure 6:
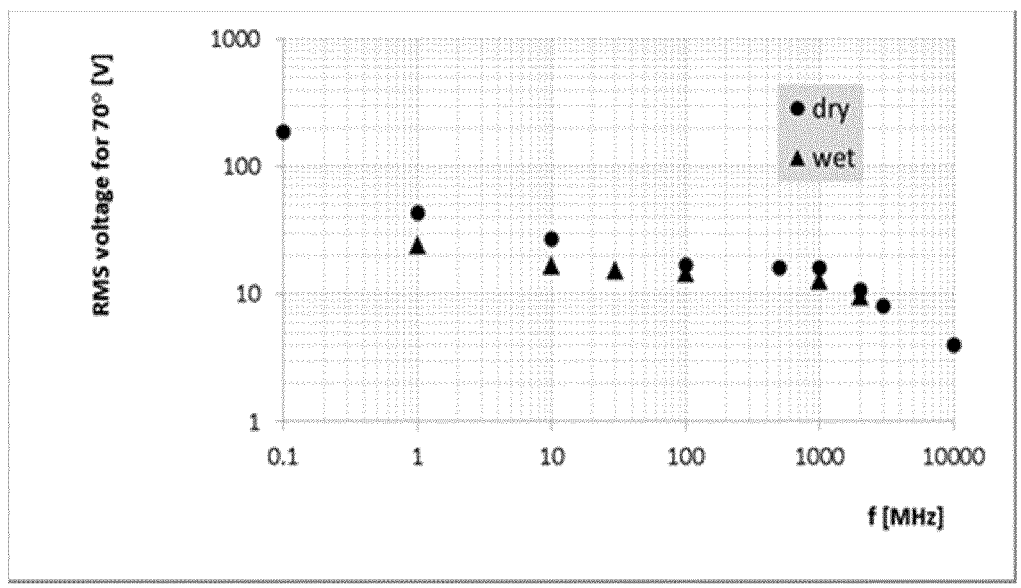
FIG. 6 shows a graph of the RMS value of the applied RF treatment voltage across the electrodes as a function of the frequency of the RF treatment voltage.

Another advantage of the use of the frequency range according to the invention is an increased efficiency of the energy conversion of the RF energy into thermal energy, resulting in a decreased RF treatment voltage required to achieve the desired thermal lesions as shown in FIG. 6. From FIG. 6 it can be seen that an RF treatment voltage lower than 20 V (RMS value) can be used when using a frequency of the RF treatment voltage in the range of 100 MHz-3 GHz.

Figure 7:
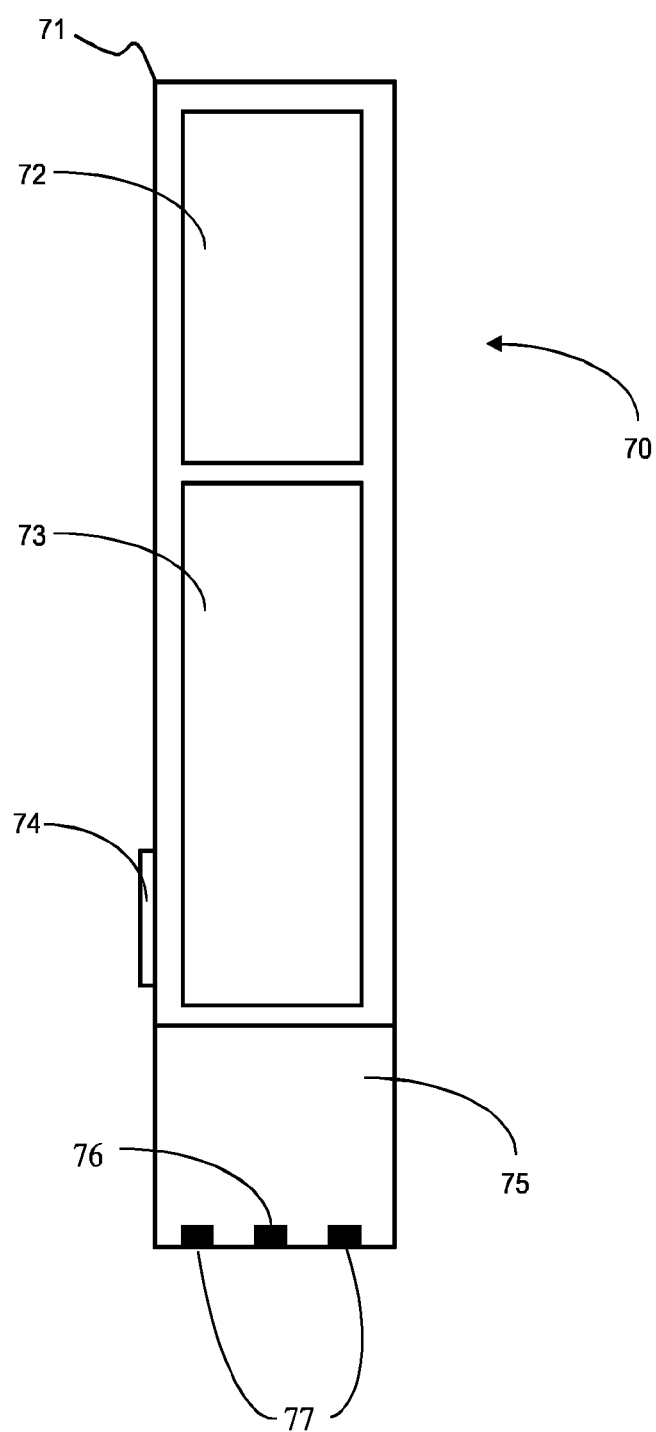
FIG. 7 schematically shows a further embodiment of a device for RF skin treatment according to the invention.

FIG. 7 schematically shows a further embodiment of a device 70 for RF skin treatment according to the invention. The device 70 comprises a housing 71, a battery 72 and an electronic module 73. The electronic module 73 may be a PCB containing sensor, an RF generator, a feedback controller, and a function generator. At the bottom, the device 70 comprises an active inner electrode 76 and an outer return electrode 77. The inner electrode 76 and outer electrode 77 may be configured as described above. The device 70 also comprises a button 74 that can be activated by the user in order to generate RF treatment pulses between the inner and outer electrodes 76 and 77. The device 70 has an elongated shape which, when suitably dimensioned, can be used as a pen which can be put into contact with the skin. This embodiment is especially useful as a home-use handheld skin treatment device for skin rejuvenation.

In the device according to the invention, a ratio between the area of the second skin contact surface of the return electrode 2 and the area of the first skin contact surface of the active electrode 1 is greater than 5. Preferably said ratio is greater than 10. By virtue of such a ratio, it is achieved that thermal lesion formation is concentrated at the skin regions immediately below the active electrodes 1, while no or no significant thermal heating of skin regions below the return electrode is caused. The use of a plurality of active electrodes allows the generation of a defined pattern of fractional thermal lesions at positions below the active electrodes. According to the invention, to achieve fractional thermal lesions, the active electrode 1 has a largest cross-sectional dimension, e.g. a diameter, less than or equal to 2 mm, preferably in a range of 200-500 microns. To achieve fractional treatment, the return electrode does not need to surround the active electrode or active electrodes. In certain embodiments, the return electrode may be arranged adjacent to the active electrodes without surrounding the active electrodes. When surrounding the active electrode or active electrodes, the return electrode may fully or partially surround the active electrode or active electrodes. When fully surrounding the active electrode or active electrodes, the return electrode may have any shape, for example annular or polygonal, such as a square or rectangular shape.

The device according to the invention may be used for treatment of skin. The device is especially useful for rejuvenation of the skin.

It is noted that, in this document, the word 'comprising' does not exclude the presence of elements or steps other than those listed, and the word 'a' or 'an' preceding an element does not exclude the presence of a plurality of such elements, and any reference signs do not limit the scope of the claims. Furthermore, the invention is not limited to the embodiments, and the invention lies in each and every novel feature or combination of features described above or recited in mutually different dependent claims.

The invention claimed is:

1. A device for RF skin treatment, comprising:
   a single active electrode arranged on an operational side of the device and having a first skin contact surface for contact with a skin of a user, which first skin contact surface has a largest cross-sectional dimension smaller than or equal to 1 mm;
   a single return electrode arranged on the operational side of the device and having a second skin contact surface for contact with the skin of the user, an area of the second skin contact surface being at least five times larger than an area of the first skin contact surface,
   wherein the single return electrode fully surrounds the single active electrode centrally positioned inside the return electrode on the operational side;
   an RF generator arranged to supply an RF treatment voltage between the active electrode and the return electrode so as to heat a skin region immediately below the active electrode to achieve deeper thermal penetration depths and wider depth to width ratios of concentrated thermal lesion formation immediately below the active electrode with substantially no thermal heating below the return electrode for RF treatment voltages less than 20V and RF frequencies in a range of 500 MHz-1.5 GHz relative to thermal penetration depths and depth-to-width ratios of concentrated thermal lesions generated with RF frequencies below 100 MHz; and wherein the device comprises an electronic controller configured to receive an input signal related to a desired lesion depth or a desired lesion depth-to-width ratio, and to control the frequency of the RF treatment voltage depending on the desired lesion depth or the desired lesion depth-to-width ratio.

2. The device according to claim 1, wherein a ratio between the area of the second skin contact surface and the area of the first skin contact surface is greater than 10.

3. The device according to claim 1, wherein the return electrode fully surrounds the active electrode on the operational side.

4. The device according to claim 1, wherein the second skin contact surface has an annular or polygonal shape.

5. The device according to claim 1, wherein the first skin contact surface has a largest cross-sectional dimension in a range of 200 microns-500 microns.

6. A device for RF skin treatment, comprising:
a single active electrode arranged on an operational side of the device and having a first skin contact surface for contact with a skin of a user, which first skin contact surface has a largest cross-sectional dimension smaller than or equal to 2 mm;
a single return electrode arranged on the operational side of the device and having a second skin contact surface for contact with the skin of the user, an area of the second skin contact surface being at least five times larger than an area of the first skin contact surface;
wherein the single return electrode fully surrounds the single active electrode centrally positioned inside the single return electrode on the operational side;
an RF generator arranged to supply an RF treatment voltage between the single active electrode and the single return electrode so as to heat a skin region immediately below the active electrode,
wherein the RF treatment voltage has a frequency of 100 MHz-3 GHz, and
wherein the RF treatment voltage has a RMS value of less than 20V.

7. The device according to claim 6, wherein the first skin contact surface has a largest cross-sectional dimension smaller than or equal to 1 mm.

8. The device according to claim 6, wherein the first skin contact surface has a largest cross-sectional dimension in a range of 200 microns-500 microns.

9. A device for RF skin treatment, comprising:
a single active inner electrode arranged on an operational side of the device and having a first skin contact surface for contact with a skin of a user, which first skin contact surface has a largest cross-sectional dimension smaller than or equal to 1 mm;
a single ring-shaped return electrode arranged to surround the active electrode and having a second skin contact surface for contact with the skin of the user, an area of the second skin contact surface being at least ten times larger than an area of the first skin contact surface such that undesired heating of the skin region below the single ring-shaped return electrode is prevented;
wherein the single active inner electrode is located in the center of the ring-shaped outer electrode;
wherein the single return electrode fully surrounds the single active electrode centrally positioned on the operational side;
an RF generator arranged to supply an RF treatment voltage between the active electrode and the return electrode so as to heat a skin region below the active electrode to achieve an optimal thermal penetration depth and a depth to width ratio,
wherein the RF treatment voltage has a frequency in a range of 1 GHz 1.5 GHz, and
wherein the RF treatment voltage has a RMS value of less than 50 V.

10. The device according to claim 9, wherein the first skin contact surface has a largest cross-sectional dimension in a range of 200 microns-500 microns.

11. The device according to claim 9, wherein a gap between a point on the inner edge of the active inner electrode and a point of the inner edge of the ring-shaped return electrode is greater than 0.1 mm.

12. The device according to claim 9, wherein a gap between a point on the inner edge of the active inner electrode and a point of the inner edge of the ring-shaped return electrode is greater than 0.2 mm.

* * * * *